United States Patent [19]
Packer

[11] 3,964,111
[45] June 22, 1976

[54] URINE CONDUCTING APPARATUS

[76] Inventor: Paul R. Packer, 140 Lockwood Ave., New Rochelle, N.Y. 10801

[22] Filed: Jan. 7, 1975

[21] Appl. No.: 539,164

[52] U.S. Cl. ................................ 4/110
[51] Int. Cl.² ........................... E03D 13/00
[58] Field of Search ............... 4/110; 128/295

[56] References Cited
UNITED STATES PATENTS

| | | | |
|---|---|---|---|
| 1,928,170 | 9/1933 | Dwork | 4/110 |
| 1,951,871 | 3/1934 | Judah | 4/110 |
| 2,382,276 | 8/1945 | Wells | 4/110 |
| 2,654,892 | 10/1953 | Szabo | 4/110 |
| 2,734,198 | 2/1956 | Kutsche | 4/110 |
| 2,878,486 | 3/1959 | Bartlett et al. | 4/110 |
| 3,419,913 | 1/1969 | Crosby | 4/110 |
| 3,495,278 | 2/1970 | Peters | 4/110 X |
| 3,643,266 | 2/1972 | Black | 4/110 X |

*Primary Examiner*—Richard E. Aegerter
*Assistant Examiner*—Charles E. Phillips

[57] ABSTRACT

A urine conducting apparatus is described which enables a woman to urinate from a standing position and which may be supported during use solely by the legs and body of the user. The urine conducting apparatus comprises an outer tapered flexible urine conductor having a wide inlet mouth contoured to envelop the perineum, and a liner adapted to fit within and cover the interior surface of the outer conductor. The inlet mouth of the conductor has a thickened rim containing embedded spring means constructed to enable the conductor to be supported within the crotch of the user in fluid tight engagement with the perineum by an inward movement of the user's legs.

7 Claims, 11 Drawing Figures

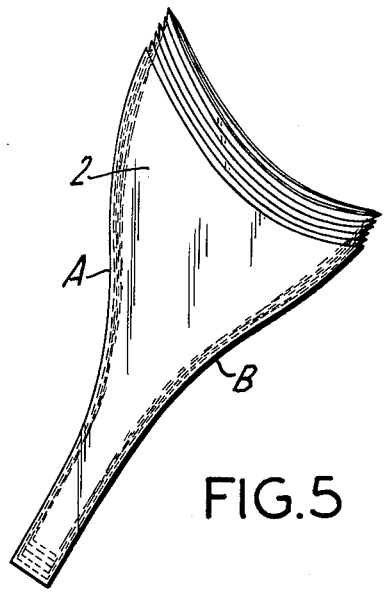
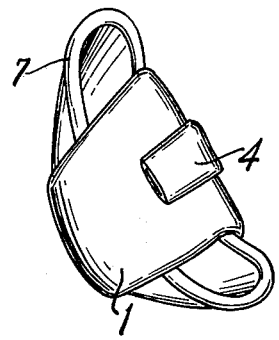
FIG.4　　　　　FIG.5　　　　　FIG.6
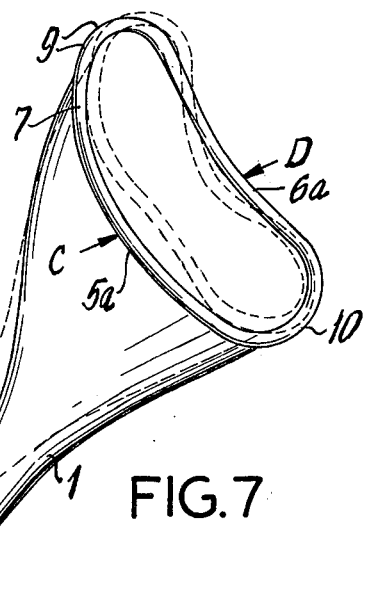
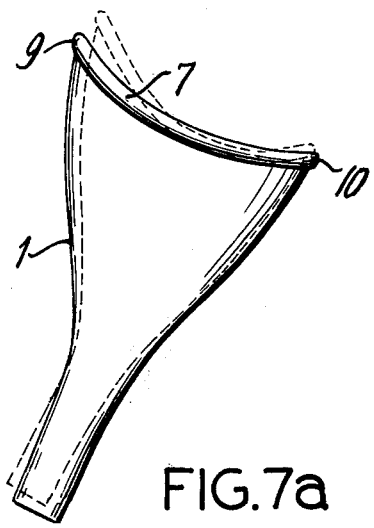
FIG.7　　　　　FIG.7a
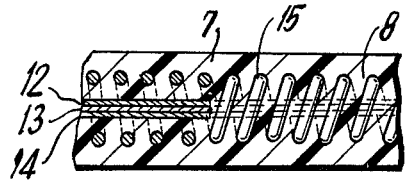
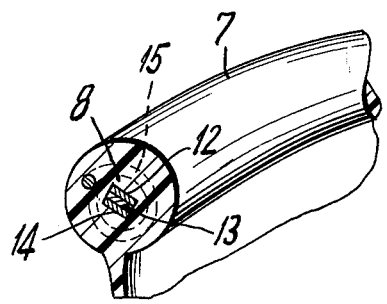
FIG.8　　　　　FIG.9

URINE CONDUCTING APPARATUS

This invention relates to feminine sanitary devices and, more particularly, to urine conducting apparatus which enables a woman to urinate from a standing position.

Such urine conducting apparatus is useful for women who wish to avoid contact with the seats of public toilets; or is useful in other situations, such as on camping trips or in a sick bed where women might prefer not to be obliged to disrobe or to sit, squat, or come in contact with unsanitary facilities in order to urinate.

Heretofore such urine conducting apparatus has been either of the type exemplified by U.S. Pat. Nos. 3,613,122 or 1,510,973, where the conductor is adapted to be inserted within the labia of the vulva in registration with the urethra; or of the type exemplified by U.S. Pat. Nos. 2,878,486 or 2,734,198 wherein the conductor is adapted to be held against the perineum.

In the former type the necessarily small mouth of the conductor makes it difficult to position the conductor accurately and limits the capacity of the conductor to accommodate large amounts of urine under considerable bladder pressure. The latter type of apparatus does not have these objections, but its larger size makes it difficult to construct an apparatus that is sufficiently compact to be portable in quantities or inexpensive enough to be disposable. Accordingly such apparatus requires frequent cleansing to be maintained in a sanitary condition. In addition, such apparatus has heretofore required that it be at least partially supported manually against the perineum.

Accordingly, it is an object of my invention to provide an improved urine conducting apparatus of the type which fits over the perineum but has permanent and disposable elements making it unnecessary for the user to carry more than one permanent element which does not require frequent cleansing.

Other objects of my invention are to provide a perineum-covering, easily portable, urine conductor which may be supported during use solely by the legs and body of the user and in which the tightness of the fluid seal between the conductor and perineum can be regulated by the movement of the legs of the user.

In general, in accord with the invention, a urine conducting apparatus is provided comprising an outer tapered urine conductor having a wide inlet mouth contoured to fit against and envelop the perineum, and having a narrow spout at the other end to direct the urine outlet flow; and a thin easily packageable and portable liner, preferably of water repellent disposable material, having the same size and configuration as the interior of the outer conductor so as to removably fit within, be supported by, and substantially cover such interior surface.

In accord with further features of the invention, the inlet mouth region of the conductor is flexibly biased to press against and be supported solely within the crotch of the user by the legs of the user. A thickened rim is provided around the contoured inlet mouth of the conductor containing spring means to assist in such self-support. Such spring means is preferably also constructed to cause the anterior and posterior ends of the conductor mouth to move cephalad against the perineum as the sides of the rim are moved toward one another by an inward movement of the legs of the user, thereby to regulate and insure a fluid tight seal between the conductor and the perineum during urination.

The invention, together with further objects, features and advantages thereof will become more readily apparent by reference to the following description taken in connection with the accompanying drawing wherein FIG. 1 is a perspective view of the urine conducting apparatus of the invention;

FIGS. 4 and 5 are side views of a plurality of disposable liners used in the urine conducting apparatus of FIG. 1 in a folded and packaged condition;

FIG. 6 is a perspective view of a preferable construction of the outer conductor of the invention in a folded condition suitable for carrying in a woman's handbag;

FIGS. 7 and 7a are perspective and side views of the urine conductor showing the cephalad movement of the anterior and posterior end portions of the inlet region as the sides of the inlet rim are moved toward one another; and FIGS. 8 and 9 are enlarged sectional views of a portion of the inlet rim showing a preferred spring means.

Figure 1:
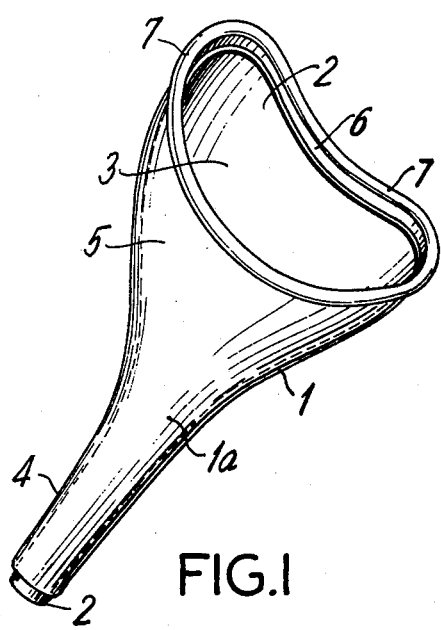
FIG. 1a is a similar perspective view of a modification of the inlet rim of the urine conducting apparatus of FIG. 1.
Figure 2:
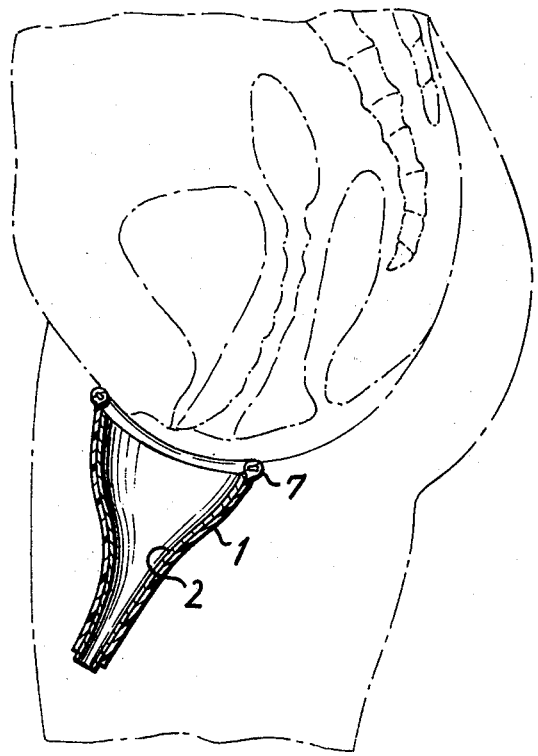
FIG. 2 is a sectional view showing the urine conducting apparatus FIG. 1 in urination position from a side view of the human body.
Figure 3:
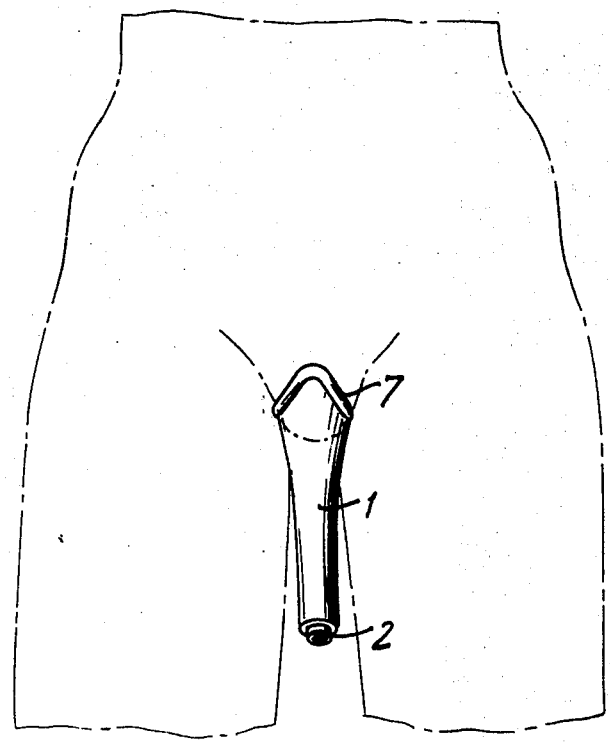
FIG. 3 is a frontal body view showing the urine conducting apparatus of FIG. 1 supported in urination position within the female crotch against the perineum by the legs of the user.

Referring to FIG. 1, the urine conducting apparatus of the invention is shown as comprising an outer conductor 1 and a thin inner liner 2. Conductor 1 has a tapered body 1a with a wide inlet mouth region 3 at one end and a narrow outlet spout 4 at the other end. Mouth region 3 is contoured to fit within the female crotch, as shown in FIG. 3, so as to cover and snugly envelop the perineum as shown in FIG. 2.

Liner 2 has the same size and tapered configuration as the interior surface of conductor 1 and is constructed to fit within, help support and be supported by and substantially entirely cover the interior surface of such conductor 1. Liner 2 is made of water repellent paper or similar material inexpensive enough to be disposable. Its tapered configuration makes it foldable longitudinally along opposite anterior and posterior edges A and B in order that several of such liners may be carried in packaged condition, one within the other, as shown in FIGS. 4 and 5. A single liner 2 is preferably made of paper that is thick enough to remain in a longitudinally extended condition when it is opened in a conical shape by pressing the folded edges toward one another, it is inserted within conductor 1.

Conductor 1 is preferably made of thin pliable plastic material, less than 0.10 inch thick, capable of being folded around the rim of its inlet mouth as shown in FIG. 6, yet sturdy enough that when unfolded into its extended position it will remain thus extended. It will be appreciated, however, that after a liner 2 is inserted within conductor 1 when the conductor is in its extended position the liner 2 will act to further support and maintain conductor 1 in a firm extended condition. While conductor 1 is preferably made foldable in order to permit it to be carried within a woman's handbag, it may alternatively be made of a firmer or thicker plastic material so as normally to remain in a semi-rigid unfoldable extended position but which is pliable enough that it may be flexed under moderate hand or leg pressure away from such normal position, returning to its original position when such pressure is removed. In particular, the opposite sides 5 and 6 of the inlet mouth region 3 are thus made flexible so as to be movable under leg pressure toward one another; and the entire outlet spout region 4 is also made similarly flexible so as to be movable under manual pressure a short distance in any direction to enable the user to direct the outlet flow in any desired direction.

Conductor 1 also has an enlarged rim 7 of circular cross section around the edge of the contoured mouth region 3. Rim 7 may be from 5/32 to ¼ inch in cross-sectional diameter and is preferably also made of plastic material so that it may be comfortably applied within the crotch of the user. Conductor 1 also contains spring means, shown as a spring assembly 8 (see FIG. 8) embedded within rim 7, for increasing the outward biasing pressure against the legs of a user when sides 5 and 6 of the inlet mouth region 3 are moved toward one another. Such inward leg movement entraps rim 7 within the flesh of the sides of the crotch and holds conductor 1 and the inserted liner 2 without further support against the perineum.

Spring assembly 8 is also preferably constructed to cause the anterior and posterior ends 9 and 10 respectively of the mouth region 3 of conductor 1 to move cephalad in an upward direction as the side regions 5 and 6 are moved toward one another as illustrated in FIGS. 7 and 7a. This causes the mouth of conductor 1 to be more tightly pressed against the anterior and posterior regions of the perineum to insure a fluid tight seal therewith in such regions. It will be appreciated that a similar fluid tight seal is maintained with the side edges of the mouth of conductor 1 because of the entrapment of the opposite sides 5a and 6a of rim 7 between the legs and the flesh of the crotch of the user.

One suitable construction for spring assembly 8 imbedded within rim 7 is shown in FIGS. 8 and 9. This spring assembly is similar to that used in the rims of contraceptive diaphragm of the type known as the Ortho diaphragm marketed under the trade mark "ALL-FLEX".

This spring assembly 8 comprises three side-by-side continuous metal leaf springs 12, 13, 14, about 1/16 inch wide, which encircle the mouth of conductor 1 within rim 7 and which are surrounded along their length by a spiral wire 15 holding the leaf springs together. The entire spring assembly 8 is molded within the plastic material of rim 7. The leaf springs 12, 13, 14 are held by wire 15 at a slight angle relative to the general plane of the mouth opening. As a consequence, a radial inward motion of the spring assembly 8 due to pressure applied at two opposing points causes a lateral displacement of this continuous spring assembly in an axial direction at points most remote from the original points of deflection. Thus, in the instant application, an inward deflection as shown by arrows C and D of the two opposite sides 5a and 6a of the rim 7 containing this spring assembly will cause an axial deflection of the anterior and posterior ends 9 and 10 of the rim 7.

Figure 1A:
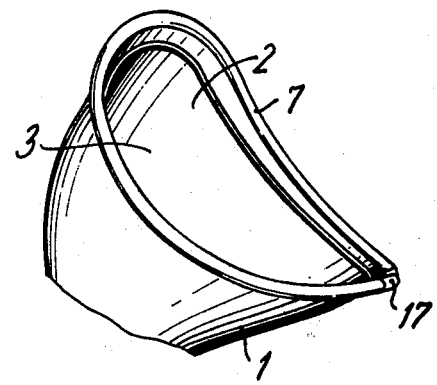

If desired this cephalad movement can be further enhanced by cutting the continuous leaf spring assembly 8 at the posterior end 10 and rejoining the severed ends at this point by a pivotal connection 17 (see FIG. 1a). Such pivotal connection 17 causes more of the lateral stress forces to be transmitted to the opposite anterior end when the sides of the spring assembly are deflected toward one another, thereby causing a greater deflection of the anterior end than would occur without such pivotal connection 17.

While the urine conducting apparatus of FIG. 1 may be made in several sizes to accommodate women of different height, weight and frame, I have determined that a conductor 1 having an inlet mouth about 4½ inches from anterior end 9 to posterior end 10 and about 3 inches from side 5 to side 6 at its widest region, and having a tapered body from mouth to spout end of about 8 inches will be suitable for the great majority of women. The corresponding dimensions of liner 2 are obviously made slightly smaller than these conductor 1 dimensions so that liner 2 may be inserted within conductor 1 yet substantially entirely cover the interior surface thereof.

It will thus be seen that the above-described conductor 1, in its preferred form, and the liner 2 may be independently carried in folded condition within a woman's handbag. In use, the conductor 1 and liner 2 are removed from the handbag, unfolded, and the liner 2 inserted within the extended conductor 1. The urine conducting apparatus thus assembled is placed against the perineum with the rim 7 inserted within the crotch while the legs of the user are slightly spread apart. An inward movement of the user's legs by a short distance will then entrap rim 7 within the crotch and the entire urine conducting apparatus may be thus self-supported. The tightness of the seal between the conductor 1 and the perineum during urination may then also be regulated by the degree of inward movement of the user's legs.

It is to be understood that while I have shown a particular embodiment of my invention, many modifications can be made; and I therefore intend by the appended claims to cover all such modifications as fall within the true spirit and scope of my invention.

What I claim is new and desire by Letters Patent of the United States is:

1. Urine conducting apparatus for use by females comprising an outer portable urine conductor having a tapered body with a wide inlet mouth at one end contoured to fit against and envelop the female perineum and having a narrow spout at the other end to direct the urine outlet flow, said conductor also having a thickened rim around its inlet mouth and its tapered body being made of thin pliable plastic material foldable around the rim when the conductor is not in use, and a thin portable and disposable liner of water repellent material having the same size and configuration as the interior surface of said conductor to removably fit within and substantially entirely cover the interior surface of said conductor, said liner being sturdy enough to help support said conductor body in extended condition when inserted within the conductor during use thereof.

2. The urine conducting apparatus of claim 1 wherein the liner comprises water repellent paper thick enough to be self-supporting in longitudinally extended condition during use thereof.

3. The urine conducting apparatus of claim 2 wherein the paper liner when separate from said outer conductor is foldable into substantially flat condition so that a plurality of such liners may be stacked one within the other in said folded condition.

4. Urine conducting apparatus for use by females comprising an outer portable urine conductor having a tapered body with a wide inlet mouth at one end contoured to fit against and envelop the female perineum and having a narrow spout at the other end to direct urine outlet flow, and a thin portable and disposable liner of water repellent material having the same size and configuration as the interior surface of said conductor to removably fit within and substantially entirely cover the interior surface of said conductor, the inlet mouth region of said conductor having a thickened rim containing inner metal spring means providing an outward stiffening spring bias to said rim, whereby said rim is flexibly biased outwardly to press tightly against the legs of a user to enable said conductor and liner to be supportable within her crotch by an inward movement of her legs while in a standing position.

5. A urine conductor for use by females comprising a tapered body having a wide inlet mouth region at one end contoured to fit snugly against and envelop the female perineum and having a narrow spout at the other end to direct the urine outlet flow, and a thickened rim around said inlet mouth edge containing internal metal spring means for providing a stiffening outward spring bias to said rim, whereby said rim presses tightly against the legs of a user to support said conductor when inserted within her crotch.

6. The urine conductor of claim 5 wherein the spring means comprises an assembly constructed to cause the anterior and posterior ends of the rim to move cephalad against the perineum as the sides of the rim are pressed toward one another by an inward movement of the legs of a user.

7. The urine conductor of claim 6 wherein the inner metal spring assembly contains a pivotal connection at the posterior end of the rim to increase the cephalad movement of the anterior end of the rim against the perineum as the sides of the rim are pressed toward one another.

* * * * *